(12) United States Patent
Landray et al.

(10) Patent No.: US 6,888,034 B1
(45) Date of Patent: May 3, 2005

(54) PROCESS FOR OXIDATION OF CYCLOHEXANE

(75) Inventors: David Paul Landray, North Yorkshire (GB); Ludovic Rick Fodor, Beaumont, TX (US); Bruce Edwin Murphree, Beaumont, TX (US); James Marvin Rung, Victoria, TX (US)

(73) Assignee: Invista North America S.A.R.L., Wilmington, DE (US)

( * ) Notice: Subject to any disclaimer, the term of this patent is extended or adjusted under 35 U.S.C. 154(b) by 0 days.

(21) Appl. No.: 10/702,255

(22) Filed: Nov. 5, 2003

(51) Int. Cl.[7] ........................ C07C 45/32; C07C 409/00; C07C 35/08

(52) U.S. Cl. ........................ 568/357; 568/358; 568/565; 568/836

(58) Field of Search ................................. 568/357, 358, 568/565, 836

(56) References Cited

U.S. PATENT DOCUMENTS

| | | | |
|---|---|---|---|
| 3,515,751 A | * 6/1970 | Oberster et al. | 560/179 |
| 3,957,876 A | 5/1976 | Rapoport et al. | |
| 6,008,415 A | * 12/1999 | Greene et al. | 568/358 |

* cited by examiner

*Primary Examiner*—Johann Richter
*Assistant Examiner*—Sikarl A. Witherspoon

(57) ABSTRACT

Process for oxidizing cyclohexane in which oxygen is contacted with cyclohexane at a pre-selected feed rate in a first reaction zone and unconsumed oxygen is contacted with cyclohexane in a second reaction zone in which the cyclohexane feed rate is lower than the pre-selected feed rate.

12 Claims, 3 Drawing Sheets

PROCESS FOR OXIDATION OF CYCLOHEXANE

FIELD OF THE INVENTION

The present invention relates to liquid phase oxidation of cyclohexane and especially to a method of decreasing oxygen content of the final off-gas in such oxidation.

BACKGROUND OF THE INVENTION

Cyclohexanol and cyclohexanone can be produced commercially from cyclohexane. The first step in such a process is oxidation of the cyclohexane by an oxygen-containing gas, e.g. air or oxygen-enriched air, to produce cyclohexanol, cyclohexanone and cyclohexyl hydroperoxide (CHHP). The mixture of cyclohexanol (A) and cyclohexanone (K) is commonly referred to as "KA" or "KA oil". The reaction is generally conducted at temperatures from about 130° C. to about 200° C. Different types of reactors are in commercial use and include single autoclaves, multiple autoclaves in series, horizontal single reactors with multiple compartments, and multistage column reactors. Air is generally used as the source of oxygen. Any unreacted oxygen (along with the nitrogen present in the air) leaves the reactor or reactors as a gaseous effluent. The gaseous effluent also contains vaporized cyclohexane and other compounds. The unreacted oxygen is commonly referred to as "oxygen leakage." The vaporized cyclohexane and other products in the gaseous effluent are condensed and recovered, and the off-gases leave the system, usually to an abatement system. The KA product is recovered from the liquid effluent from the reactor or reactors, and the unreacted cyclohexane is recycled.

It has been observed that the lower the oxygen leakage from a reactor, the higher the formation of undesirable byproducts and hence the lower is the yield to desirable products. In the oxidation of cyclohexane, the yield of cyclohexanone, cyclohexanol and cyclohexyl hydroperoxide, can be optimized by operating at high oxygen leakage (i.e. concentration of unreacted oxygen in the mixture of cyclohexane free oxygen, nitrogen and other gases and vapors). Unfortunately, at oxygen leakage concentration in excess of 8 vol %, unsafe flammable mixtures can form in the effluent gas stream. Therefore, as a margin of safety the oxygen leakage is usually kept below 4 vol %. Higher oxygen leakage also means that the air being fed to the reactor(s) is not being fully utilized. In other words, the process requires more air, which leads to increased compression cost. In addition, an increased volume of off-gas causes increased cost for off-gas treatment. U.S. Pat. No. 3,957,876 (Rapoport & White) teaches a method to reduce oxygen leakage from a cyclohexane oxidation process through the use of a so-called clean up reaction zone. The Rapoport & White patent discloses a process of cyclohexane oxidation in a column reactor that has a number of perforated trays for contacting an oxygen-containing gas with liquid cyclohexane. The column has two zones. Liquid cyclohexane enters the top part of the top zone, denoted "clean up" zone, and flows downward through the trays in the clean up zone where it contacts the gaseous effluent from the bottom zone in a counter-current fashion. The liquid effluent from the clean up zone comprising liquid cyclohexane, CHHP, K and A enters the top part of the bottom zone and flows downward through the trays in the bottom zone here it contacts an oxygen-containing gas in a counter-current fashion. The oxygen containing gas enters the bottom part of the bottom zone. The bottom zone accomplishes the major part of the oxidation reaction. A liquid effluent comprising cyclohexane, CHHP, K and A is withdrawn from the bottom part of the bottom zone. The clean up zone allows additional consumption of oxygen by reacting it with cyclohexane and thus produces an off-gas that contains oxygen of adequately low concentration so that an explosion hazard can be avoided.

One disadvantage in the Rapoport & White method is that the entire flow of cyclohexane is contacted with the gaseous effluent from the bottom zone. Since the concentration of oxygen is significantly low in the gaseous effluent to be treated, a high reaction temperature, and/or catalyst is required to consume enough oxygen to reduce the concentration of oxygen in the off-gas to an acceptable level. The entire cyclohexane flow, therefore, has to be heated to this high temperature. Since the same hot cyclohexane is used for reaction in the bottom zone, the reaction temperature in the bottom zone is high. It is well known in the art that high reaction temperature in the cyclohexane oxidation process is detrimental to yield to desirable products since high temperature is favorable for producing undesirable byproducts.

It would, therefore, be desirable to have a cyclohexane oxidation process in a column reactor, as taught by Rapoport & White, that would have low oxygen concentration in the off-gas and that would allow a lower reaction temperature in the bottom zone compared to that described in the Rapoport & White patent. It would also be desirable to have processes to accomplish low oxygen concentration in the off-gas, said processes being applicable to other types of reactors used in cyclohexane oxidation, e.g. single autoclaves, multiple autoclaves in series, and horizontal single reactors with multiple compartments.

SUMMARY OF THE INVENTION

The present invention provides such processes. In one embodiment of this invention, a column reactor is operated in a way that only a portion of the liquid cyclohexane is fed to a clean up reaction zone where it contacts a gaseous effluent from a primary reaction zone (bottom zone). The remaining portion of the cyclohexane flow is fed directly to the top part of the primary reaction zone. Hence the temperature of this remaining portion of cyclohexane flow can be any desirable temperature independent of the temperature of the clean up reaction zone. Thus this present invention should be able to achieve a yield of desirable products that is higher than the corresponding yield from the method described by Rapoport & White.

In another embodiment of the invention, a clean up reaction zone is included in the process in which a portion of the total cyclohexane flow is contacted with the gaseous effluent from a primary reaction zone. A portion of the oxygen in the gaseous effluent to be treated is consumed in a clean up reactor and hence a low concentration of oxygen should be achieved in the off-gas. The remaining portion of the cyclohexane flow is fed directly to the primary reaction zone. In addition to decreasing oxygen concentration in the off-gas and increasing yield to desirable product, this invention is also expected to provide stability of operation.

The present invention is, therefore, a cyclohexane oxidation process that comprises:
  introducing into a primary reaction zone liquid cyclohexane at a first flow rate and an oxygen-containing gas, thereby contacting said cyclohexane and said oxygen containing gas, optionally in the presence of a cyclohexane oxidation catalyst, to produce a primary liquid reaction product that comprises cyclohexyl hydroperoxide (CHHP), cyclohexanone (K) and cyclohexanol (A), withdrawing from said primary reaction zone said liquid reaction product, withdrawing from said primary reaction zone a primary reaction zone gas that comprises unreacted gaseous cyclohexane and 0.5 to 6.0 vol % oxygen, introducing into a clean-up reaction zone the primary reaction zone gas and liquid cyclohexane at a second flow rate that is lower than said first flow rate, thereby contacting the primary reaction gas with the liquid cyclohexane to produce a clean-up reaction product that comprises CHHP, K and A, and withdrawing from said clean-up reaction zone a clean-up reaction zone gas that comprises oxygen in a concentration that is lower than that in the primary reaction zone gas.

BRIEF DESCRIPTION OF THE DRAWING

The Drawing consists of 3 figures.

DETAILED DESCRIPTION OF THE INVENTION

Figure 1:
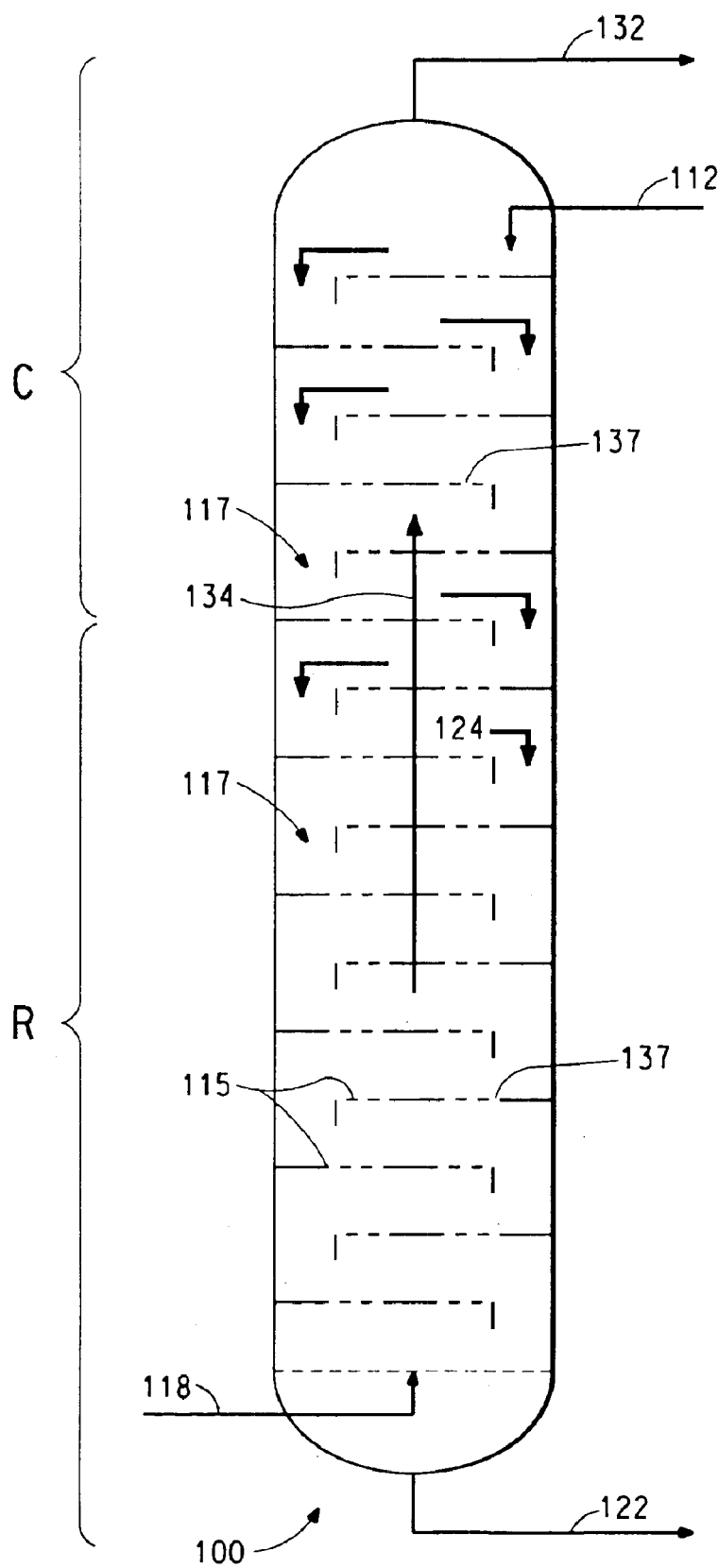
FIG. 1 depicts a block diagram of the process of using a clean up reaction zone as taught by Rapoport & White for a column oxidizer.

Referring now to FIG. 1, there is shown an apparatus 100 that illustrates the teachings of the Rapoport and White patent. In apparatus 100, the top zone of the column indicated by a bracket identified as C is the clean-up reaction zone and the bottom zone of the column indicated by a bracket identified as R is the primary reaction zone. A stream of hot liquid cyclohexane (112) enters the top part of the clean-up reaction zone (C) and it flows across the trays (115) and downward through the down-comers (117). In doing so it contacts in a counter-current fashion a stream of gaseous effluent (134) coming from the primary reaction zone (R) as in a normal tray column. The liquid effluent from the clean-up zone (124) comprising liquid cyclohexane, CHHP, K and A enters the top part of the primary reaction zone (R) and flows across the trays and downward through the down-corners of trays in the primary reaction zone, where it contacts an oxygen-containing gas in a counter-current fashion. The oxygen-containing gas (118) enters the bottom part of the primary reaction zone and flows upward through holes (137) in the trays (115) of the column. The oxygen-containing gas may also be split and introduced in multiple locations in the primary reaction zone. A liquid effluent (122) comprising cyclohexane, CHHP, K and A is withdrawn from the bottom part of the primary reaction zone. The mass flow rates of liquid (e.g. in streams 112, 124 & 122) through the clean up reaction zone and the primary reaction zone are essentially the same (considering negligible loss as vapor).

Figure 2:
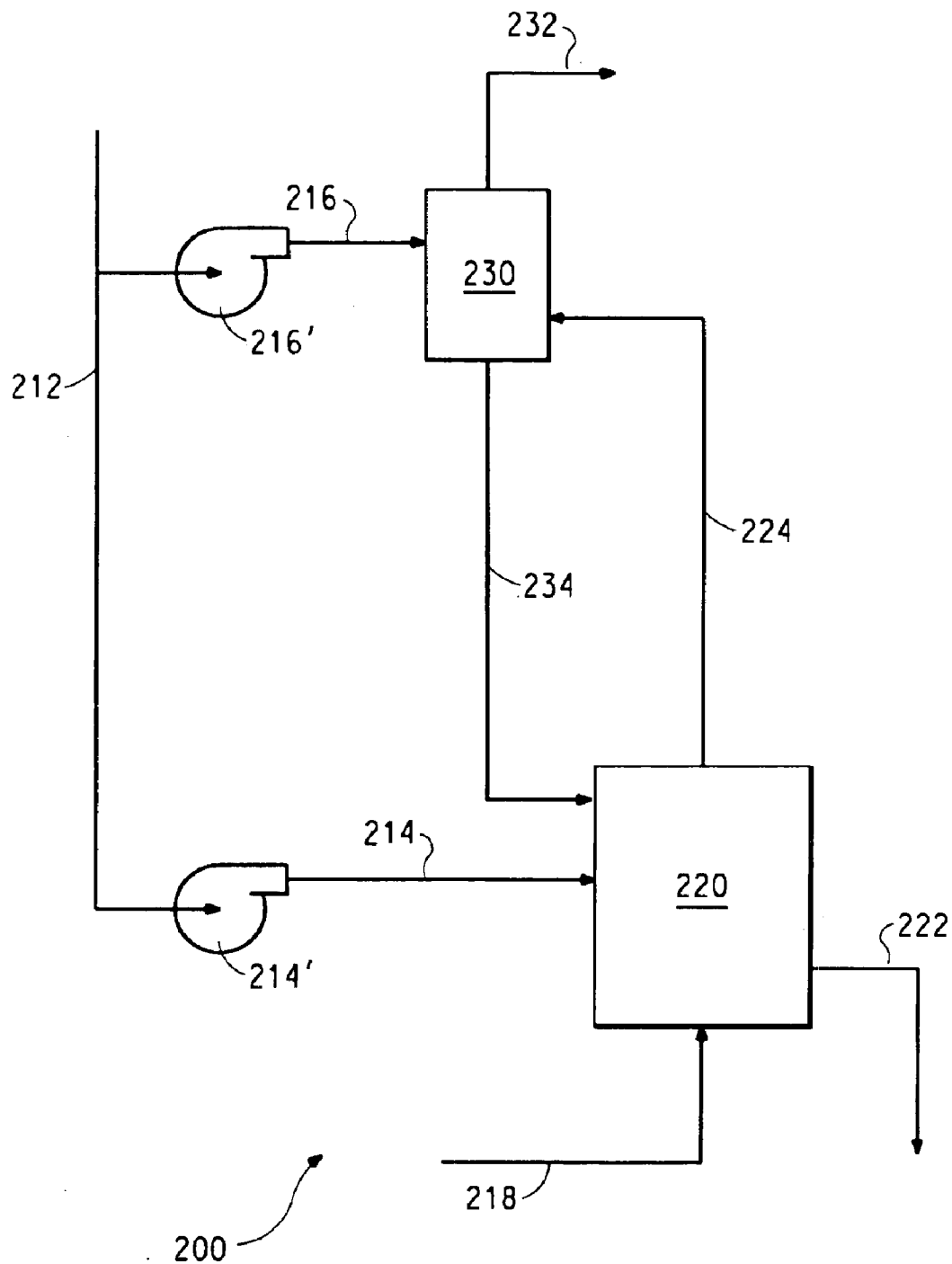
FIG. 2 depicts a block diagram of a process embodying the present invention in which the primary reaction zone and the clean up reaction zone can be selected independently from the group comprising single autoclaves, multiple autoclaves in series, horizontal single reactors with multiple compartments and multistage column reactors.

Referring now to FIG. 2, one embodiment 200 of the present invention is depicted. A stream comprising liquid cyclohexane (212) is divided into two streams: one stream at a first flow rate (214) and another stream at a second flow rate (216). Streams 216 and 214 can be preheated and can be delivered by pumps 216' & 214' or regulated by automatic valves. The liquid cyclohexane in stream (212) may contain fresh cyclohexane and/or liquid cyclohexane recycled from any subsequent part of the process. Stream (214) is contacted with an oxygen-containing gas stream (218) in a primary reaction zone (220). A stream of cyclohexane oxidation catalyst, e.g. soluble salts of cobalt or chromium might be introduced (not shown) directly to the primary reaction zone (220), clean up zone (230), or premixed with liquid cyclohexane in stream (214) and/or (216). The primary liquid reaction product (222) comprising cyclohexane, CHHP, K and A, and the primary reaction zone gas (224) comprising unreacted oxygen exit the primary reaction zone.

The primary reaction zone (220) can be a single autoclave optionally equipped with a device for providing agitation (not shown). The liquid cyclohexane (214) is allowed to contact the oxygen-containing gas (218) in the autoclave for a desired reaction time. The primary liquid reaction product (222) and the primary reaction zone gas (224) exit the autoclave.

The primary reaction zone can comprise two or more autoclaves in series, each autoclave optionally equipped with an agitation device, and with or without arrangement for cooling between autoclaves (not shown). The liquid cyclohexane (214) would enter the first autoclave in the series and the primary liquid reaction product (222) would exit the last autoclave. The transfer of liquid from one autoclave to the next can be carried out by using a pump, pressure differential or by gravity flow. The oxygen-containing gas (218) can be split and introduced into each autoclave. Gaseous effluents from each autoclave can be combined to form the primary reaction zone gas (224).

The primary reaction zone (220) can be a multistage column in which liquid flows across trays and downward through down-corners of trays, and gas flows upward through holes in the trays. The volume between the trays could be liquid filled, or partially liquid filled. Different types of trays can be used including but not limited to sieve, bubble cap, and valve trays. Both the liquid cyclohexane (214) and the oxygen-containing gas (218) can be split and introduced in multiple locations in the column. The primary liquid reaction product (222) would exit the bottom of the column. The primary reaction zone gas (224) would exit the top of the column.

The primary reaction zone (220) might be a column reactor in which liquid flows upward with the gas in co-current fashion through trays having holes. Both the liquid cyclohexane (214) and the oxygen-containing gas (218) can be split and introduced in multiple locations in the column. The primary liquid reaction product (222) would exit at the top of the column. The primary reaction zone gas (224) would also exit the top of the column.

The primary reaction zone (220) might also be a horizontal vessel with two or more compartments inside (not shown). The liquid cyclohexane stream (214) would enter one end of the vessel, and the primary liquid reaction product (222) would exit the other end, with liquid flowing from one compartment to the next as overflow and/or underflow. Each compartment can be optionally equipped with an agitation device. The oxygen-containing gas (218) can be split and introduced into each compartment. Gaseous effluents from each compartment can be combined to form the primary reaction zone gas (224).

The oxidation of cyclohexane in the primary reaction zone (220) takes place at an elevated temperature and pressure. The temperature is generally in the range of 130 to 200 degrees C. The pressure is generally in the range of 800 to 2500 kPa. The source of heat for the reaction can be partly the heat content of a preheated cyclohexane stream (214) and partly the heat of reaction. The liquid contact time or residence time in the primary reaction zone (220) should be in the range of 2 to 90 minutes per stage.

The primary liquid reaction product (222) containing the product of oxidation is processed through additional reactors and separation units (not shown) in which the unreacted cyclohexane is recovered and recycled as part of the liquid cyclohexane stream (212). The primary reaction zone gas (224) from the primary reaction zone (220) is optionally processed in an entertainment separator unit (not shown) in which any liquid cyclohexane present as droplets or mist is allowed to coalesce and separate from the gas phase.

The primary reaction zone gas (224), optionally processed as above, is contacted with liquid cyclohexane at a second flow rate (216) in a clean-up reaction zone (230). The second flow rate (216) is lower than the first flow rate (214). A liquid clean-up reaction product (234) containing the product of oxidation in the clean-up reaction zone and a gaseous effluent, namely the clean-up reaction zone gas (232), comprising unreacted oxygen, exits the clean-up reaction zone (230). The concentration of oxygen in the clean-up reaction zone gas (232) is lower than the concentration of oxygen in the primary reaction zone gas (224).

The clean-up reaction zone (230) might be a single autoclave optionally equipped with a device for providing agitation (not shown). The liquid cyclohexane at second flow rate (216) and the optionally processed primary reaction zone gas (224) are allowed to contact each other in the autoclave for a desired reaction time. The clean-up reaction product (234) and the clean-up reaction zone gas (232) exit the autoclave (230).

The clean-up reaction zone (230) might comprise two or more autoclaves in series (not shown), with each autoclave optionally equipped with an agitation device (not shown) and with or without arrangement for cooling between any two autoclaves (not shown). The liquid cyclohexane at second flow rate (216) would enter the first autoclave in the series and the clean-up reaction product (234)-would exit the last autoclave. The optionally processed primary reaction zone gas (224) can be split and introduced into each autoclave. Gaseous effluents from each autoclave can be combined to form the clean-up reaction zone gas (232).

The clean-up reaction zone (230) might be a multistage column in which liquid flows across trays downward through down-corners of trays, and gas flows upward through holes in the trays. Both the liquid cyclohexane at a second flow rate (216) and the optionally processed primary reaction gas (224) might be split and introduced in multiple locations in the column. The liquid clean-up reaction product (234) would exit the bottom of the column. The clean-up reaction zone gas (232) would exit the top of the column.

The clean-up reaction zone (230) might also be a horizontal vessel with two or more compartments inside (not shown). The liquid cyclohexane at second flow rate (216) would enter one end of the vessel and the clean-up reaction product (234) would exit the other end of the vessel. Each compartment can be optionally equipped with an agitation device (not shown). The primary reaction zone gas (224) can be split and introduced into each compartment. Gaseous effluents from each compartment can be combined to form the clean-up reaction zone gas (232).

Multiple vessels of any of the above types of reactors in parallel can be used as the clean-up reaction zone.

The temperature in the clean-up reaction zone (230) is independent of the temperature in the primary reaction zone (220). The temperature is generally in the range of 130 to 200 degrees C. The pressure is generally in the range of 800 to 2500 kPa. The cyclohexane fed to the clean-up reaction zone can be preheated or unheated, but preferably unheated. The source of heat in the clean-up reactor can be the heat content of liquid cyclohexane stream (216), the heat content of the off-gases and the heat of reaction. The desired liquid residence time in the clean-up reaction zone is 2 to 90 minutes per stage.

The clean-up reaction zone gas (232) is generally processed through an off-gas-processing unit (not shown). The clean-up reaction product (234) from the clean-up reaction zone can be combined with liquid cyclohexane of first flow rate (214) introduced into the primary reaction zone (220) or directly introduced into the primary reaction zone (220). Multiple units of clean-up reaction zones in parallel can be used to treat primary reaction zone gas (not shown).

Figure 3:
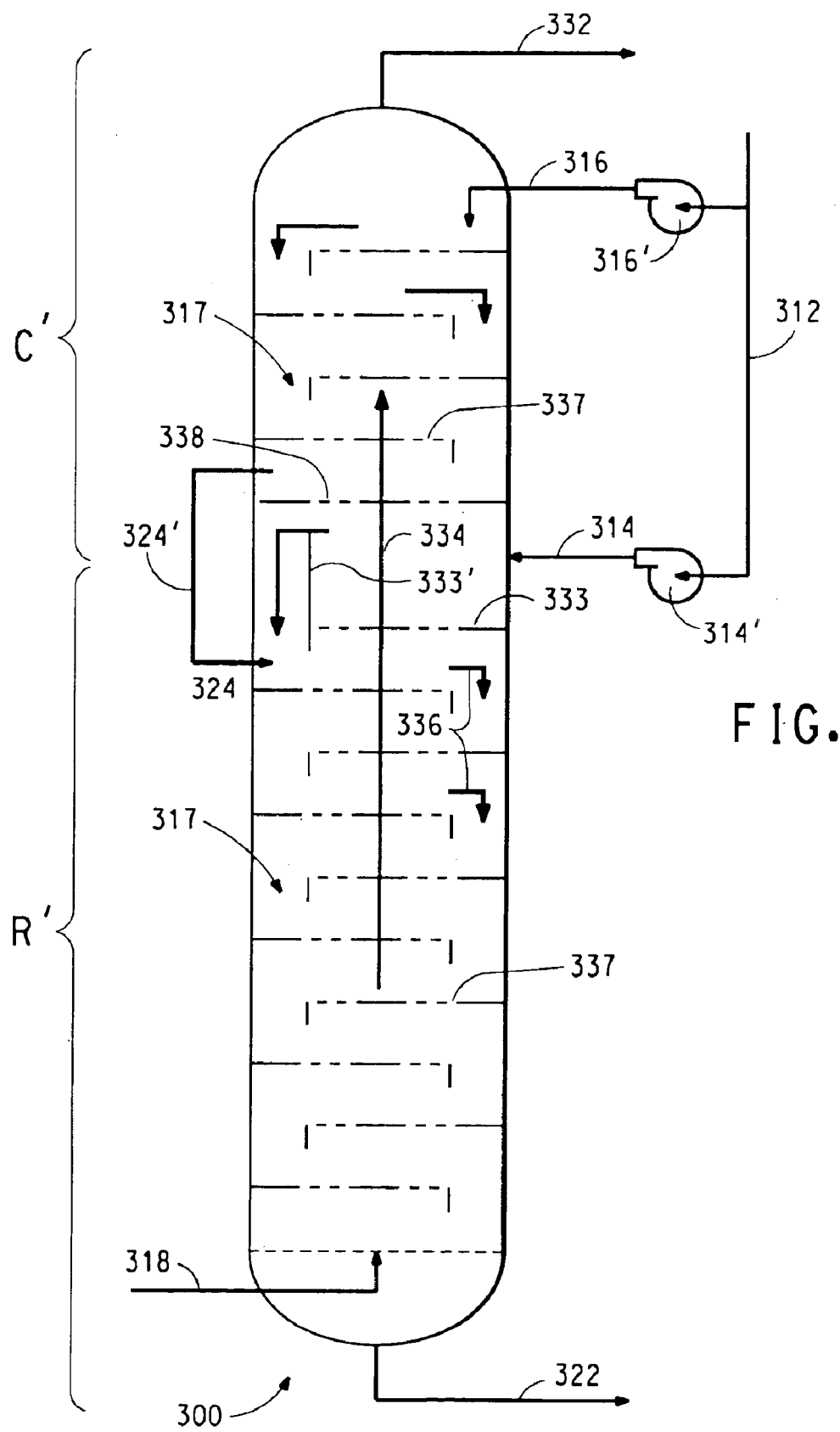
FIG. 3 depicts a block diagram of a process embodying the present invention in which the primary reaction zone and the clean up reaction zone are two zones of a column oxidizer.

Referring now to FIG. 3, there is shown another apparatus 300 for practicing the present invention. The apparatus 300 comprises a column, the top zone of which, as indicated by a bracket identified as C', is the clean-up reaction zone and the bottom zone as indicated by a bracket identified as R' is the primary reaction zone. A sealed tray (338) separates the clean-up reaction zone and the primary reaction zone. The sealed tray allows the primary reaction zone gas (334) from the bottom of this tray to flow upward through holes (337) in it, but the liquid from above this tray is not allowed to flow down through it. A stream of liquid cyclohexane (312) is split into two parts: stream of first flow rate 314 and stream of second flow rate 316. Stream 316, optionally preheated, enters the top part of the clean-up reaction zone (C'), and it flows across the trays and downward through down-corners (317) of the trays so that it contacts in a counter-current fashion the primary reaction zone gas (334) coming upward from the primary reaction zone (R'). Gas flows upward in the clean up reaction zone through holes in trays (337). The liquid effluent from the clean up reaction zone, namely the clean-up reaction product (324), comprising liquid cyclohexane, CHHP, K and A is withdrawn from the bottom of the clean-up reaction zone and is then introduced at the top part of the primary reaction zone (R'). This flow arrangement can be through an external pipeline (324') or through an internal double down-corner (not shown). The flow of cyclohexane (314), after preheating, is introduced at the top part of the primary reaction zone. The top tray (333) in the primary reaction zone is equipped with an extended weir (333') so that a substantial volume of cyclohexane is accumulated above tray 333 before overflowing weir 333'. The combined liquid streams (336=314+324) flow across the trays and downward through down-corners (317) of trays in the primary reaction zone and contact in a counter-current fashion an oxygen-containing gas that flows upward through holes (337) in the trays. The oxygen-containing gas (318) enters the bottom part of the primary reaction zone. The oxygen-containing gas can also be introduced in multiple locations in the primary reaction zone (not shown). The primary liquid reaction product (322), comprising cyclohexane, CHHP, K and A, is withdrawn from the bottom part of the primary reaction zone. The mass flow rate of liquid in the primary reaction zone is significantly higher than the mass flow rate in the clean up reaction zone.

What is claimed is:

1. A cyclohexane oxidation process that comprises
   (a) introducing into a reaction zone, a first stream of liquid cyclohexane at a first flow rate and an oxygen-containing gas, thereby contacting said first stream of cyclohexane and said oxygen containing gas, optionally in the presence of a cyclohexane oxidation catalyst, to produce a primary liquid reaction product that comprises cyclohexyl hydroperoxide (CHHP), cyclohexanone (K) and cyclohexanol (A),
   (b) withdrawing from said primary reaction zone said liquid reaction product,
   (c) withdrawing from said primary reaction zone a primary reaction zone gas that comprises unreacted gaseous cyclohexane and 0.5 to 6.0 vol % oxygen,
   (d) introducing into a clean-up reaction zone the primary reaction zone gas and a second stream of liquid cyclohexane at a second flow rate that is lower than said first flow rate of the first stream of cyclohexane, thereby containing the primary reaction zone gas with the second stream of liquid cyclohexane to produce a clean-up reaction product that comprises CHHP, K and A, and
   (e) withdrawing from said clean-up reaction zone a clean-up reaction zone gas that comprises oxygen in a concentration that is lower than the oxygen concentration in the primary reaction zone gas.

2. The process of claim 1 wherein the clean-up reaction zone gas comprises oxygen at a concentration below 2.0 vol %.

3. The process of claim 1 wherein the clean-up reaction zone comprises two or more reaction vessels in series.

4. The process of claim 1, wherein the clean-up reaction zone comprises two or more reaction vessels in parallel.

5. The process of claim 1, wherein the primary reaction zone and the clean-up reaction zone comprise compartments of a single column wherein the primary reaction zone is separated from the clean-up reaction zone by a tray comprising a series of holes, the tray adapted, to prevent liquid from flowing down through the tray and to allow gas to flow up through the series of holes.

6. The process of claim 5, wherein liquid from the clean-up reaction zone is transferred to the primary reaction zone via a pipe external to the column.

7. The process of claim 5, wherein liquid from the clean-up reaction zone is transferred to the primary reaction zone via an internal down-corner in the column.

8. The process of claim 1, wherein the temperature of the clean-up reaction zone is in the range of 130° C. to 200° C.

9. The process of claim 1, wherein the temperature of the primary reaction zone is in the range of 130° to 200° C.

10. The process of claim 1, wherein the mass flow rate in the primary reaction zone is higher than the mass flow rate in the clean-up reaction zone.

11. The process of claim 1, wherein the first stream of cyclohexane and the oxygen containing gas are contacted in the presence of a cyclohexane oxidation catalyst.

12. The process of claim 11, wherein the cyclohexane oxidation catalyst comprises soluble salts of at least one metal selected from the group consisting of cobalt and chromium.

* * * * *